(12) United States Patent
Saito et al.

(10) Patent No.: US 11,859,235 B2
(45) Date of Patent: Jan. 2, 2024

(54) SENSOR, DETECTION METHOD, REAGENT AND KIT

(71) Applicant: KABUSHIKI KAISHA TOSHIBA, Tokyo (JP)

(72) Inventors: Tatsuro Saito, Kawasaki Kanagawa (JP); Yoshiaki Sugizaki, Fujisawa Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 95 days.

(21) Appl. No.: 17/199,380

(22) Filed: Mar. 11, 2021

(65) Prior Publication Data

US 2022/0081702 A1     Mar. 17, 2022

(30) Foreign Application Priority Data

Sep. 15, 2020   (JP) ................... 2020-154717

(51) Int. Cl.
*C12Q 1/46*         (2006.01)

(52) U.S. Cl.
CPC ......... *C12Q 1/46* (2013.01); *G01N 2333/918* (2013.01)

(58) Field of Classification Search
None
See application file for complete search history.

(56) References Cited

U.S. PATENT DOCUMENTS

| | | | |
|---|---|---|---|
| 5,624,831 A * | 4/1997 | Vu Khue | G01N 33/54393 435/177 |
| 5,654,178 A * | 8/1997 | Fitzpatrick | G01N 33/5308 530/391.3 |
| 2010/0227345 A1 * | 9/2010 | LeJuene | C12Q 1/34 435/20 |
| 2016/0354812 A1 * | 12/2016 | Sovesky | B08B 7/04 |
| 2020/0158720 A1 * | 5/2020 | Whitten | C12Q 1/44 |
| 2020/0300804 A1 | 9/2020 | Saito et al. | |
| 2021/0080426 A1 | 3/2021 | Saito | |
| 2022/0081702 A1 * | 3/2022 | Saito | C12Q 1/46 |

FOREIGN PATENT DOCUMENTS

| | | |
|---|---|---|
| JP | 3160111 U | 6/2010 |
| JP | 2020-153783 A | 9/2020 |
| JP | 2021-43169 A | 3/2021 |

OTHER PUBLICATIONS

A. de Souza et al., "Chemical composition and acetylcholinesterase inhibitory activity of essential oils of Myrceugenia yrcioides (Cambess.) O. Berg and Eugenia riedeliana O. Berg, Myrtaceae," Brazilian J. of Pharmacognosy, vol. 20, No. 2, pp. 175-179, (2010).
I. Fakih et al., "Sensitive Precise pH Measurement with Large-Area Graphene Field-Effect Transistors at the Quantum-Capacitance Limit," Physical Review Applied, vol. 8, pp. 044022-1 to -7 (2017).
J.S. Kang et al., "A Soluble Acetylcholinesterase Provides Chemical Defense against Xenobiotics in the Pinewood Nematode." PLoS ONE, vol. 6, No. 4, e19063, 7 pages (2011).
K. Hostettmann et al., "Natural Product Inhibitors of Acetylcholinesterase," Current Organic Chemistry, vol. 10, No. 7, 24 pages (2006).
K. Dhananjayan et al., "Molecular Docking Studies and in-vitro Acetylcholinesterase Inhibition by Terpenoids and Flavonoids," Asian J. Research Chem., vol. 6, No. 11, pp. 1011-1017 (2013).
P.K. Mukherjee et al., "Acetylcholinesterase inhibitors from plants," ScienceDirect, Phytomedicine vol. 14, pp. 289-300 (2007).
T. Matsuo et al., "Ion Sensitive Semiconductor Electrode," Japanese Journal of Medical Electronics and Biological Engineering, vol. 21, No. 7, pp. 510-516 (1983).
International Search Report for International Application No. PCT/JP2019/014706 dated May 14, 2019, 2 pages.

\* cited by examiner

*Primary Examiner* — Blaine Lankford
(74) *Attorney, Agent, or Firm* — Finnegan, Henderson, Farabow, Garrett & Dunner, LLP (57) ABSTRACT

According to one embodiment, a sensor for detecting a target substance in gas a sample includes a target substance uptake unit that brings an acetylcholine aqueous solution into contact with a gas sample to dissolve a target substance in the gas sample into the acetylcholine aqueous solution, a reaction unit that holds acetylcholinesterase and brings the solution delivered from the target substance uptake unit into contact with the acetylcholinesterase, and a detection unit that measures a change in an amount of acetylcholine decomposition product produced in the solution delivered from the reaction unit.

12 Claims, 7 Drawing Sheets

SENSOR, DETECTION METHOD, REAGENT AND KIT

CROSS-REFERENCE TO RELATED APPLICATIONS

This application is based upon and claims the benefit of priority from Japanese Patent Application No. 2020-154717, filed Sep. 15, 2020, the entire contents of which are incorporated herein by reference.

FIELD

Embodiments described herein relate generally to a sensor, a detection method, a reagent, and a kit.

BACKGROUND

A sensor and a detection method for detecting a target substance are required to detect the target substance with high sensitivity.

An object of the present invention is to provide a sensor and a detection method that are capable of detecting a target substance with higher sensitivity.

DETAILED DESCRIPTION

In general, according to one embodiment, a sensor for detecting a target substance in gas a sample comprises a target substance uptake unit that brings an acetylcholine aqueous solution into contact with a gas sample to dissolve a target substance in the gas sample into the acetylcholine aqueous solution, a reaction unit that holds acetylcholinesterase and brings the solution delivered from the target substance uptake unit into contact with the acetylcholinesterase and a detection unit that measures a change in an amount of acetylcholine decomposition product produced in the solution delivered from the reaction unit.

Hereinafter, various embodiments will be described with reference to the drawings. Each figure is a schematic view for promoting understanding of the embodiment, and its shape, dimensions, ratio, etc., may differ from the actual ones, but these can be appropriately modified in consideration of the following explanation and known techniques.

In the present specification, a term "gas sample" refers to a sample made of a gaseous target substance, or a sample having a target substance in the state of a gas, a liquid, an aerosol, or a particulate substance typified by PM2.0 mixed with a gas.

First Embodiment

Figure 1:
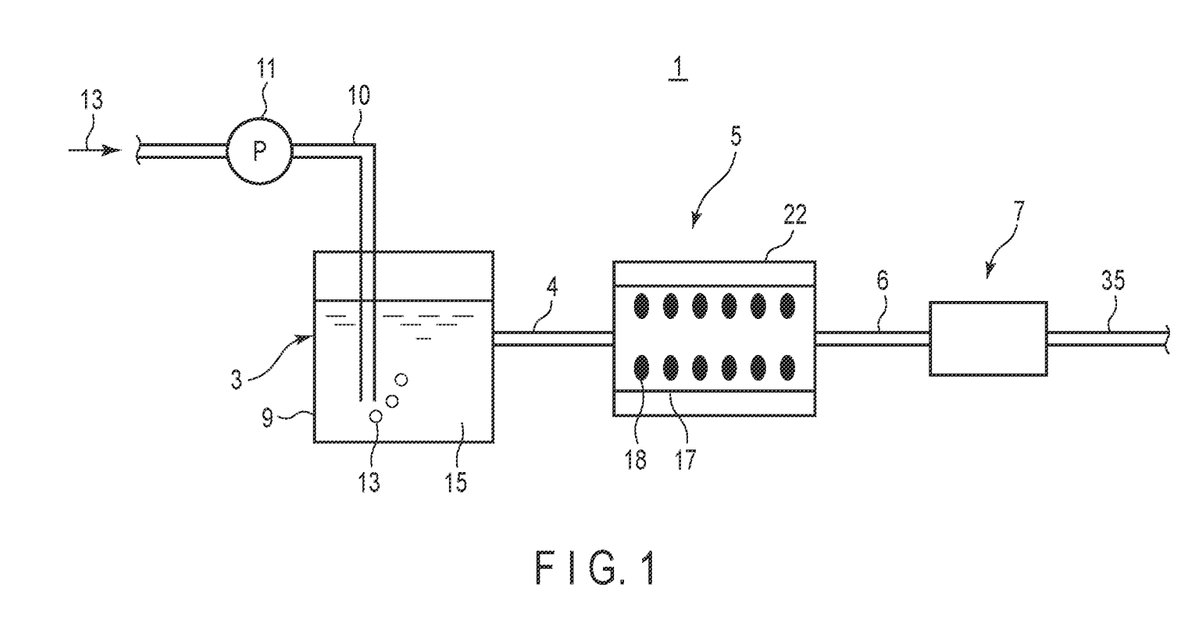
FIG. 1 is a schematic view showing an example of a sensor according to a first embodiment.

A sensor according to the first embodiment is a sensor for detecting a target substance in a gas sample. As shown in FIG. 1, a sensor 1 includes a target substance uptake unit 3, a reaction unit 5 connected to a conduit 4 extending from the target substance uptake unit 3, and a detection unit 7 connected to a conduit 6 extending from the reaction unit 5. As will be described in detail later, the target substance in the gas sample is taken into an acetylcholine aqueous solution in the target substance uptake unit 3, and the aqueous solution is taken from the target substance uptake unit 3, passing through the respective conduits 4 and 6, and delivered to the reaction unit 5 and the detection unit 7 in this order.

The target substance uptake unit 3 includes a container 9 holding an acetylcholine aqueous solution 15. A conduit 10 for a gas sample is connected to the container 9. A pump 11 is interposed in the conduit 10. By driving the pump 11, a gas sample 13 indicated by the arrow, which may contain the target substance, is delivered to the container 9 through the conduit 10. The gas sample 13 delivered to the container 9 comes into contact with the acetylcholine aqueous solution 15 in the container 9. At this time, when the gas sample 13 contains the target substance, the target substance is incorporated into the acetylcholine aqueous solution 15.

The contact between the gas sample 13 and the acetylcholine aqueous solution 15 can be carried out by bubbling, for example, by blowing the gas sample 13 into the acetylcholine aqueous solution 15 as shown in FIG. 1. Further, another method may be used, for example, by spraying the gas sample 13 on the liquid surface of the acetylcholine aqueous solution 15.

The acetylcholine aqueous solution 15 in contact with the gas sample 13 is delivered from the target substance uptake unit 3 to the reaction unit 5 through the conduit 4. The reaction unit 5 includes a reaction vessel 17 to which the conduit 4 is connected. The reaction vessel 17 is a vessel that can hold a liquid, for example, acetylcholinesterase 18 is immobilized and held. A heater 22 for heating the solution is provided on the outer peripheral surface of the reaction vessel 17. In the reaction vessel 17, the acetylcholine aqueous solution 15 delivered from the target substance uptake unit 3 and acetylcholinesterase are brought into contact with each other. When the target substance is contained in the acetylcholine aqueous solution 15 at this time, acetylcholine, acetylcholinesterase, and the target substance coexist in the reaction vessel 17. The solution 19 that has passed through the reaction vessel 17 is delivered from the reaction vessel 17 to the detection unit 7 through the conduit 6.

Hereinafter, the chemical reaction of acetylcholine, acetylcholinesterase, and the target substance in the reaction vessel 17 will be described in detail.

First, when acetylcholinesterase and acetylcholine coexist in the absence of a target substance, the acetylcholine decomposition reaction represented by the following chemical formula (1) proceeds.

Formula (1)

Figure 2A:
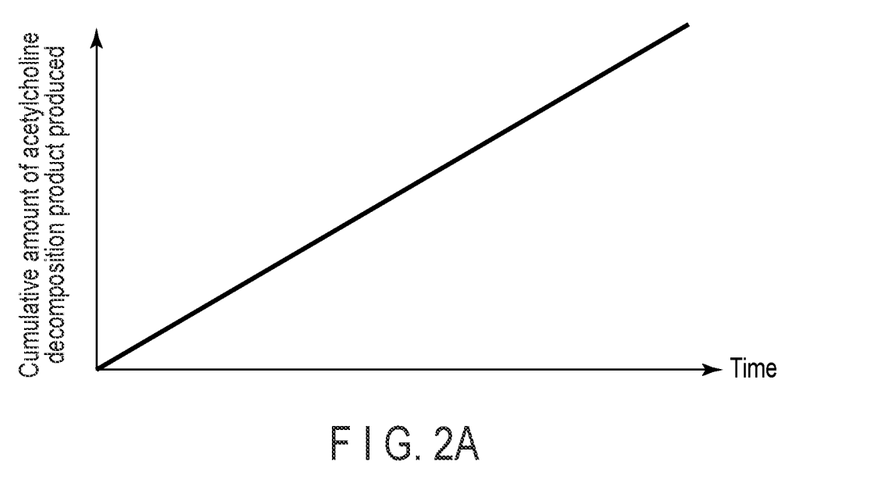
FIG. 2A is a schematic view showing a change over time of a cumulative amount of acetylcholine decomposition product produced when acetylcholine is continuously supplied in a fixed amount in a mixed system of acetylcholine and acetylcholinesterase.

From the above formula (1), it can be seen that when a certain amount of acetylcholine is continuously supplied, an acetylcholine decomposition product (that is, choline and acetic acid) is produced in an amount commensurate with the amount of acetylcholine supplied (see FIG. 2A).

Figure 2B:
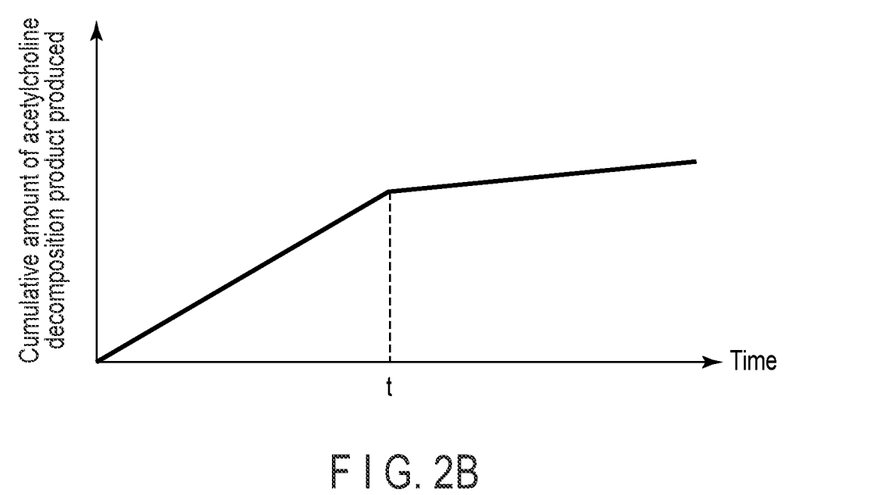
FIG. 2B is a schematic view showing a change over time of a cumulative amount of acetylcholine decomposition product produced when limonene is added to the mixed system shown in FIG. 2A at time t.

The reaction of the above formula (1) is a chemical reaction in which acetylcholine acts as a substrate and acetylcholinesterase acts as an enzyme. In general, it is known that a chemical reaction using an enzyme is inhibited by a specific chemical substance for each enzyme, and the reaction rate is reduced or the reaction is stopped. The chemical substance is hereinafter referred to as an "inhibitor". Here, in the mixed system of acetylcholinesterase and acetylcholine shown in FIG. 2A, when the inhibitor starts to be contained from time t, the cumulative amount of acetylcholine decomposition product after time t changes, that is, the slope of the graph decreases (see FIG. 2B). Therefore, by monitoring the decomposition rate of acetylcholine in the mixed system, it is possible to detect whether or not an inhibitor is present in the mixed system.

Acetylcholinesterase can be immobilized in the reaction vessel 17 by a granular immobilization method, a liquid immobilization method, or the like. Any acetylcholinesterase can be used. For example, acetylcholinesterase derived from electric eel can also be used. In addition, acetylcholinesterase way be an apoenzyme or a holoenzyme. When the acetylcholinesterase is an apoenzyme, a corresponding cofactor is contained in the acetylcholine aqueous solution 15, and the cofactor is supplied to the reaction vessel 17 holding the acetylcholinesterase.

Further, in the enzymatic reaction represented by the above formula (1), it is preferable that the reaction vessel 17 is heated by the heater 22 and the acetylcholinesterase in the reaction vessel 17 is further activated at around 37° C.

Although acetylcholinesterase is previously immobilized in the reaction vessel 17 of the reaction unit 5, an acetylcholinesterase aqueous solution may be held in another supply system and the acetylcholinesterase aqueous solution may be supplied to the reaction vessel 17.

Figure 3:
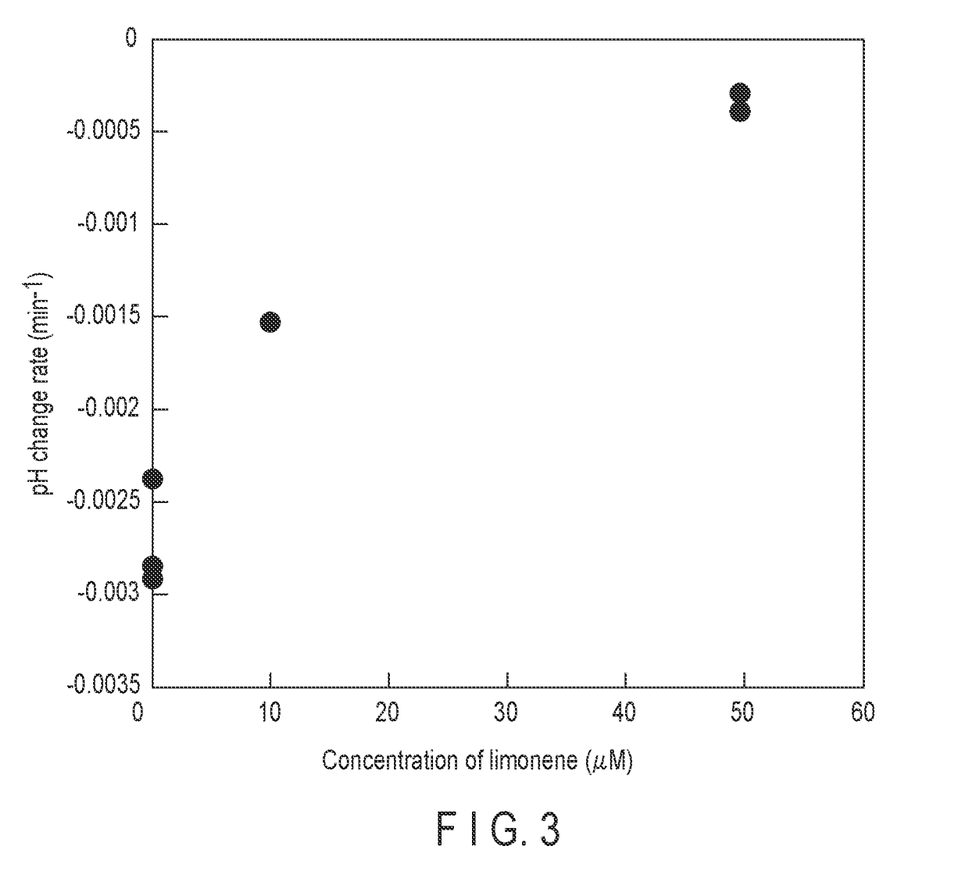
FIG. 3 is a view showing an inhibitory effect of limonene on the acetylcholine decomposition reaction of acetylcholinesterase.

The target substance to be detected by the sensor according to the present embodiment is an inhibitor against the acetylcholine decomposition reaction of acetylcholinesterase. Examples of this inhibitor include limonene. As shown in FIG. 3, it has been confirmed that the addition of limonene to the mixed system of acetylcholine and acetylcholinesterase reduces the pH change rate of the mixed system. As will be described later, the reduction in the pH change rate of the mixed system indicates that the decomposition rate of acetylcholine has decreased, and that limonene is an inhibitor against the enzyme acetylcholinesterase. Examples of the inhibitor other than limonene against the acetylcholine decomposition reaction of acetylcholinesterase include terpenoids such as ambrein and pinene, flavonoids such as luteolin, alkaloids such as galantamine, and glycosides such as Cynatroside A.

Figure 4:
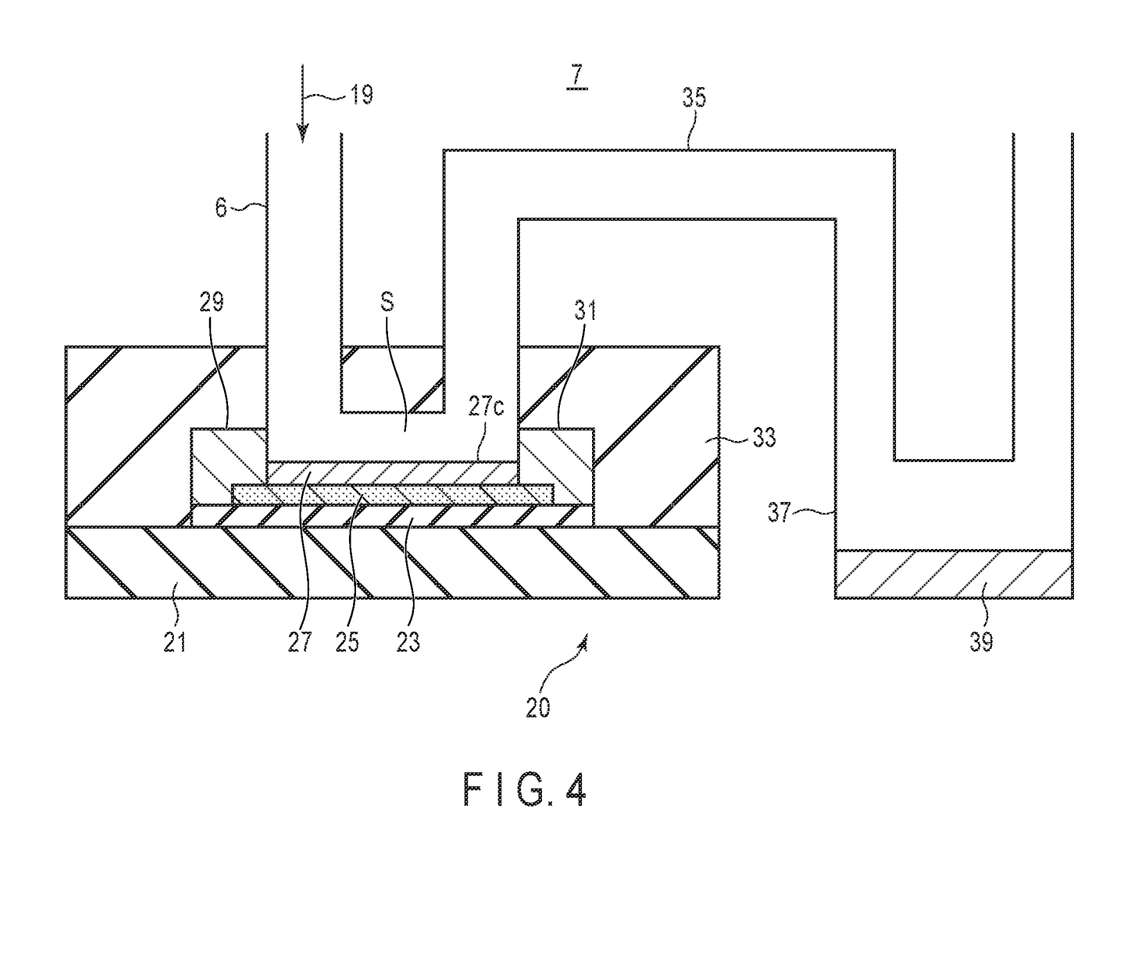
FIG. 4 is a schematic cross-sectional view showing a detection unit of the first embodiment.

Hereinafter, the structure of the detection unit of the sensor according to the first embodiment will be described in detail with reference to FIG. 4.

The detection unit 7 includes a sensing element 20 and an electrode tank 37. The sensing element 20 includes a graphene field-effect transistor (graphene FET). That is, the graphene FET includes a substrate 21, an insulating film 23 arranged on the surface of the substrate 21, graphene 25 arranged on the insulating film 23, a sensitive film 27 arranged on the graphene 25, a source electrode 29 connected to one end of the sensitive film 27, a drain electrode 31 connected to the other end of the sensitive film 27, and a protective film 33 covering the substrate 21 including the source electrode 29 and the drain electrode 31. The protective film 33 is provided with a rectangular space S above a main surface 27c of the sensitive film 27, and the main surface 27c is exposed to the space S. The space S on the source electrode 29 side is connected to the conduit 6 on the reaction unit 5 side. The space S on the drain electrode 31 side is connected to the conduit 35, and the electrode tank 37 is formed in the middle of the conduit 35. A gate electrode 39 is arranged in the electrode tank 37. The solution 19 that has passed through the reaction vessel 17 is delivered to the space S through the conduit 6 as shown by the arrow, comes into contact with the main surface 27c of the sensitive film 27, passes through the conduit 35 and then through the electrode tank 37, comes into contact with the gate electrode 39 therein, and is discharged to the outside.

The substrate 21 has, for example, a rectangular plate shape. The material of the substrate 21 is, for example, silicon, glass (SiC, etc.), ceramics (SiN, etc.), a polymer material, or the like. The substrate 21 may have a laminated structure in which an insulator layer is provided on a conductor layer. The size of the substrate 21 is not limited, and for example, the thickness of the substrate 21 can be about 1 mm. The length and width thereof may be selected so as to have a desired size according to the application of the sensor 1.

The sensitive film 27 is a pH detection element, and is an ion-sensitive film made of, for example, $SiO_2$, SiN, or a metal oxide film such as $Al_2O_3$ or $Ta_2O_3$. However, the sensitive film 27 is not limited to the pH detection element, and other elements that detect changes in physical properties due to binding or proximity to acetylcholine or its decomposition product may be adopted. As materials constituting other elements, for example, carbon materials such as graphene, diamond, or carbon nanotubes; layered compounds such as molybdenum disulfide ($MoS_2$) or tungsten diselenide ($WSe_2$), titanium disulfide ($TiS_2$), or phosphorus (P); or electrochemically stable materials in a water oxidation-reduction region such as gold (Au), platinum (Pt), or silver (Ag) can be used. The sensitive film 27 may be, for example, at least a single atomic layer, but may be a plurality of layers. Alternatively, the sensitive film 27 may have the shape of nanowires or nanotubes.

The desired length of the sensitive film 27 can be selected as desired according to the application, but the length from one end on the source electrode 29 side to the other end on the drain electrode 31 side may preferably be, for example, from 10 nm to 1 mm. Here, assuming that a direction from the source electrode 29 side to the drain electrode 31 side is a first direction, and a direction orthogonal to the first direction, in which the detection unit 7 is viewed in cross section, is a second direction, it is preferable that the sensitive film 27 is formed so that the length of the main surface 27c in the second direction is longer than the length of the upper rectangular space S in the second direction, or the length of the space S in the second direction and the length of the main surface 27c in the second direction are equal. With such a configuration, the ratio of the laminated portion of the sensitive film/channel portion that comes into contact with the solution in the second direction can be increased, and the detection sensitivity can be improved.

As shown below, the effect of the dimensions of the sensitive film 27 described above has been confirmed by manufacturing sensors A and B and comparing detection sensitivity between both the sensors.

The sensor A includes a substrate, a rectangular sensitive film made of graphene having a length of 30 µm in the second direction, a source electrode connected to one end of the sensitive film, a drain electrode connected to the other end of the sensitive film, and an insulating film covering each electrode and having a rectangular space above the sensitive film, the space having a length in the second direction of 34 µm.

The sensor B includes a substrate, a rectangular sensitive film made of graphene having a length of 30 µm in the second direction, a source electrode connected to one end of the sensitive film, a drain electrode connected to the other end of the sensitive film, and an insulating film having a rectangular space above the sensitive film covering each electrode, the space having a length in the second direction of 10 µm.

A current value flowing between the gate electrode and the drain electrode has been measured using the sensors A and B. As samples, solutions with different concentrations of chlorine ions are held on each of the sensors, and the amount of change in the current value before and after replacement of the samples has been calculated.

As a result, the current value of the sensor A has changed by about 10%. On the other hand, the current value of the sensor B has changed by about 4%, and it has therefore been confirmed that the use of the sensor A provides about twice the amount of change in the current value of the sensor B. Therefore, it has been confirmed that by forming the sensitive film so that the length of the main surface of the sensitive film in the second direction is longer than the length of the rectangular space above the sensitive film in the second direction or so that the length of the space in the second direction and the length of the main surface of the sensitive film in the second direction are equal, the detection sensitivity as a sensor can be improved.

The materials of the source electrode 29, the drain electrode 31, and the gate electrode 39 are, for example, a metal such as gold (Au), silver (Ag), copper (Cu), palladium (Pd), platinum (Pt), nickel (Ni), titanium (Ti), chromium (Cr), or aluminum (Al); or a conductive substance such as zinc oxide (ZnO), indium tin oxide (ITO), IGZO, or a conductive polymer.

The insulating film 23 and the protective film 33 are formed of, for example, an insulating material. The insulating material is, for example, ceramics such as an oxide film or a nitride film; or an insulating polymer such as polyimide.

The graphene FET constituting the sensing element 20 can be manufactured by a semiconductor process. For example, it can be manufactured as follows.

First, the insulating film 23 for preventing electric discharge is formed on the substrate 21. This step may be omitted when the substrate 21 itself is insulating.

Next, the graphene 25 is formed on the insulating film 23. As a method of forming graphene, for example, transfer from graphite or a CVD method can be used. When transfer or the like is used, graphene having a pattern formed by a printing technique or the like may be laminated. The graphene is then patterned. In this patterning step, a base for forming graphene may be formed in advance, and then graphene 25 may be selectively formed by, for example, the CVD method or the like.

Further, after the graphene 25 is formed, the source electrode 29 and the drain electrode 31 are formed at both ends of the graphene 25. Thereafter, the sensitive film 27 is formed on the graphene 25, and the protective film 33 is further formed on the surface of the substrate 21 so as to cover the source electrode 29 and the drain electrode 31. The protective film 33 processes the space S and the like by using lithography. The space S and the like may be formed by lift-off using a sacrificial layer or the like.

In addition to the sensing element 20, the detection unit 7 further includes, for example, a circuit including a power supply that applies a voltage between the source electrode 29 and the drain electrode 31, and to the gate electrode 39, and an ammeter that measures a current value flowing between the source electrode 29 and the drain electrode 31 (neither is shown). These may be provided, for example, in the substrate 21. The detection unit 7 may also include a pad electrode connected to the source electrode 29 and the drain electrode 31. Further, one sensing element or a plurality of sensing elements may be arranged on one substrate 21.

Hereinafter, the operation of the detection unit including the graphene FET described above will be described in detail.

In the first embodiment, the sensitive film 27 is a pH-sensitive film, and the surface potential of the sensitive film 27 changes according to the pH value of the solution 19 that has passed through the reaction vessel 17. Further, the surface potential of the sensitive film 27 can also be changed by the gate electrode 39. The surface potential of the sensitive film 27 also changes the potential of the graphene 25 in contact with the sensitive film 27. When the power supply applies a constant voltage between the source electrode 29 and the drain electrode 31 that are arranged at the ends of the graphene 25, the current value flowing through the graphene 25 according to the potential given to the graphene 25 changes depending on the potential of the sensitive film 27. Based on this change in the current value, the presence/absence of the target substance in the gas sample described later is detected.

In the present embodiment, since the flow rate of the sensor 1 is set to be a constant amount per unit time, the supply amount of acetylcholine to the reaction unit 5 per unit time is constant. In such sensor 1, when the target substance is not contained in the sample, an amount of acetylcholine decomposition product produced in the reaction unit 5 is constant per unit time, so that the pH value of the solution 19 delivered from the reaction unit 5 is also constant. As a result, the surface potential of the sensitive film 27, which is a pH-sensitive film, shows a constant value, and the current value flowing through the graphene 25 in contact with the sensitive film 27 is also constant.

On the other hand, when the target substance is contained in the gas sample, the target substance inhibits the acetylcholine decomposition reaction, so that an amount of acetic acid, which is an acetylcholine decomposition product, decreases, resulting in an increase in the pH value of the solution 19. The change in the pH value of the solution 19 changes the surface potential of the sensitive film 27, causing a change in the potential of the graphene 25 in contact with the sensitive film 27. The change in the potential of the graphene 25 is measured by an ammeter as a change in the current value between the source electrode 29 and the drain electrode 31.

The detection unit 7 of the sensor 1 is not limited to the graphene FET, and may include, for example, another charge detection element, an ion-selective field effect transistor (ISFET), a CCD, another pH detection element, a glass electrode, and the like. However, since the graphene FET is a sensing element that has high mobility and can measure with high mobility, even when the surface potential change of the sensitive film 27 due to the change in pH value is small, the graphene FET can detect it as a large change in the current value, and can provide a more sensitive sensor.

According to the first embodiment described above, by monitoring the change of the produced amount of the acetylcholine decomposition product in the enzymatic reaction between acetylcholine and acetylcholinesterase at the detection unit 7, the presence/absence of the target substance in the gas sample and the amount of the target substance according to the magnitude of the change amount can be detected with high accuracy. In particular, even when the target substance is a substance having difficulty of causing change in physical properties of the sensitive film 27 as it is, for example, a substance having high hydrophobicity or a substance having no or little polarity, the sensor according to the first embodiment can detect even such a substance, with high sensitivity by detecting the enzymatic reaction inhibitory effect of the target substance.

Conventionally, as a sensor for detecting a target substance, a sensor for detecting a target substance which is an inhibitor against an enzymatic reaction between acetylthiocholine and acetylcholinesterase has been known. Such a sensor has optically detected a target substance by absorbance measurement or the like, by decomposing the substrate acetylthiocholine by the enzyme acetylcholinesterase to produce thiocholine, and then allowing thiocholine to react with DTNB (5,5'-dithiobis (2-nitrobenzoic acid)) to develop color.

However, even when DTNB for a color-developing reaction is applied to choline and acetic acid generated by the enzymatic reaction between acetylcholine and acetylcholinesterase as in the first embodiment, color development does not occur. Therefore, it has been difficult for conventional sensors to detect the presence of an inhibitor, that is, a target substance, in the enzymatic reaction between acetylcholine and acetylcholinesterase. Further, conventionally, thiocholine do not have sufficient enzyme selectivity, and it has sometimes been decomposed by an enzyme other than acetylcholinesterase, such as butyrylcholinesterase. When an enzyme, other than acetylcholinesterase, that can decompose thiocholine is mixed into a sample or the like as an impurity, thiocholine is decomposed even if the enzyme reaction of acetylcholinesterase is inhibited by the target substance, so that there has been a risk that the reaction inhibitory effect of the target substance is not confirmed, failing to detect the target substance.

In the first embodiment, acetylcholine is used as a substrate for an enzymatic reaction to detect the inhibitory effect of a target substance. Acetylcholine has high enzyme selectivity, so that the influence of degrading enzymes other than acetylcholinesterase (e.g., butyrylcholinesterase) can be reduced. As a result, the target substance can be detected with higher accuracy than the conventional detection method using thiocholine.

Further, as compared with a configuration of the sensor 1 in which an acetylcholinesterase aqueous solution is held in another supply system and the acetylcholinesterase aqueous solution is supplied to the reaction vessel 17, the configuration of the sensor 1 in which the acetylcholinesterase is immobilized in the reaction unit 5 can reduce the amount of acetylcholinesterase used by using the sensor 1 because there is no outflow of acetylcholinesterase. In addition, the number of parts of the sensor 1 can be further reduced by not providing another supply system. That is, the sensor 1 having a configuration in which acetylcholinesterase is immobilized in the reaction unit 5 is preferable in that simpler measurement can be performed and cost can be reduced during manufacturing and use.

On the other hand, as compared with the configuration of the sensor 1 in which acetylcholinesterase is immobilized in the reaction unit 5, the configuration of the sensor 1 in which the acetylcholinesterase aqueous solution is held in another supply system and the acetylcholinesterase aqueous solution is supplied to the reaction vessel 17 is preferable in that it is easier to handle when the sensor 1 is reused. This is because even when acetylcholinesterase is inactivated by the inhibitory effect of the target substance, an operation of reactivating the acetylcholinesterase or an operation of replacing the immobilized acetylcholinesterase can be omitted by supplying unreacted acetylcholinesterase to the reaction unit 5.

Second Embodiment

Figure 5:
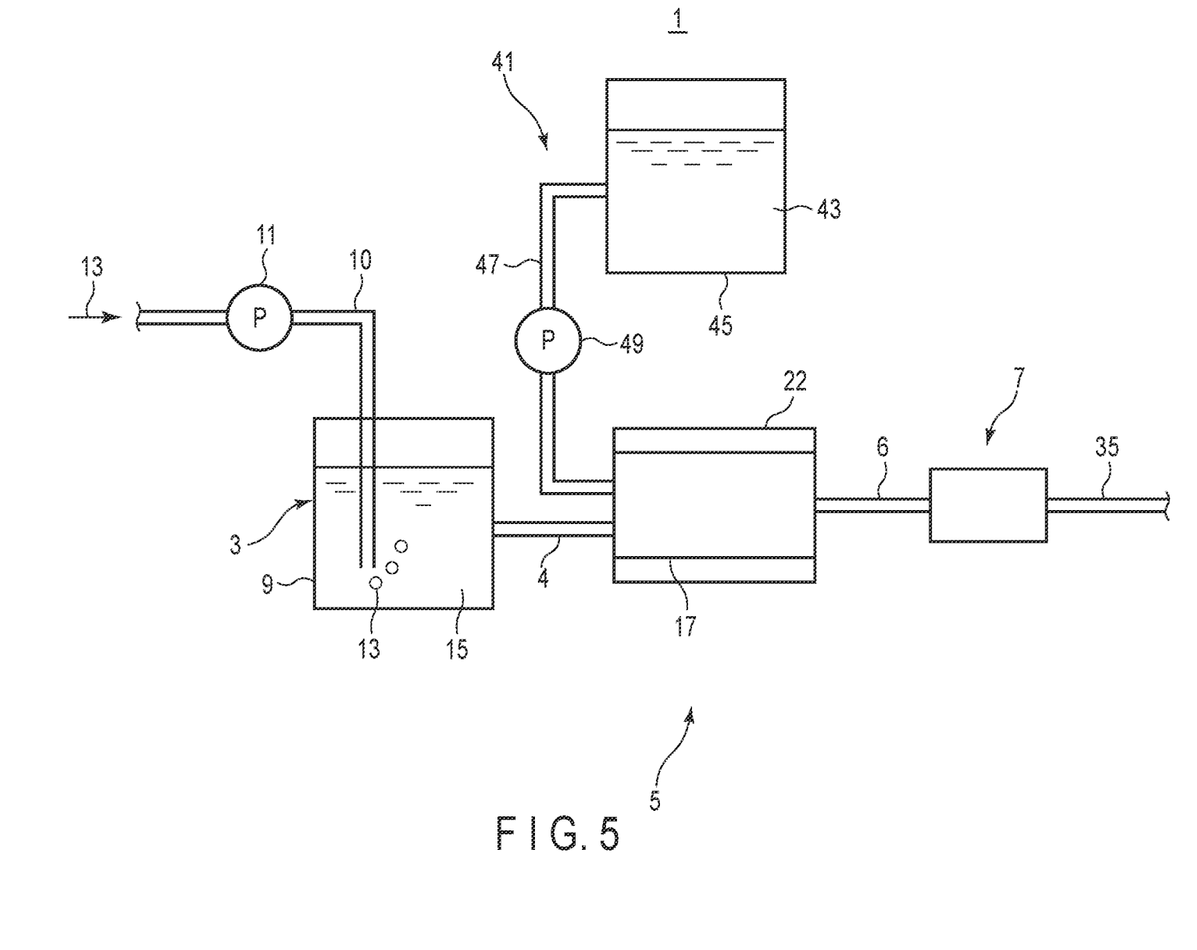
FIG. 5 is a schematic view showing an example of a sensor of a second embodiment.

A sensor according to the second embodiment will be described with reference to FIG. 5.

A sensor 1 includes a target substance uptake unit 3, a reaction unit 5 connected to a conduit 4 extending from the target substance uptake unit 3, a liquid supply unit 41 connected to the reaction unit 5 through a conduit 47, and a detection unit 7 connected to a conduit 6 extending from the reaction unit 5.

The target substance uptake unit 3 includes a container 9 holding an acetylcholinesterase aqueous solution 51. A conduit 10 for a gas sample is connected to the container 9. A pump 11 is interposed in the conduit 10. By driving the pump 11, a gas sample 13 indicated by the arrow, which may contain the target substance, is delivered to the container 9 through the conduit 10. The gas sample 13 delivered to the container 9 comes into contact with the acetylcholinesterase aqueous solution 51 in the container 9. At this time, when the gas sample 13 contains the target substance, the target substance is incorporated into the acetylcholinesterase aqueous solution 51.

The acetylcholinesterase aqueous solution 51 in contact with the gas sample 13 is delivered from the target substance uptake unit 3 to the reaction unit 5 through the conduit 4. The reaction unit 5 includes a reaction vessel 7 to which the conduit 4 is connected. The reaction vessel 17 is a vessel that can hold a liquid.

The liquid supply unit 41 includes a liquid storage unit 45 holding an acetylcholine aqueous solution 43. The liquid storage unit 45 is connected to the reaction vessel 17 through the conduit 47. A pump 49 is interposed in the conduit 47, and by driving the pump 49, the acetylcholine aqueous solution 43 in the liquid storage unit 45 is supplied to the reaction vessel 17 through the conduit 47. In the reaction vessel 17, the acetylcholinesterase aqueous solution 51 delivered from the target substance uptake unit 3 and the acetylcholine aqueous solution 43 delivered from the liquid storage unit 45 are brought into contact with each other. When the target substance is contained in the acetylcholinesterase aqueous solution 51 in this time, acetylcholine, acetylcholinesterase, and the target substance coexist in the reaction vessel 17. The solution 19 that has passed through the reaction vessel 17 is delivered from the reaction vessel 17 to the detection unit 7 through the conduit 6.

The detection unit 7 has a structure similar to that of the first embodiment described above.

According to the second embodiment having such a configuration, as in the first embodiment described above, by monitoring the change in the acetylcholine decomposition product in the enzymatic reaction between acetylcholine and acetylcholinesterase at the detection unit 7, the presence/absence of the target substance in the gas sample and the amount of the target substance according to the magnitude of the change amount can be detected with high accuracy. In particular, even when the target substance is a substance having difficulty of causing change in physical properties of the sensitive film 27 as it is, for example, a substance having high hydrophobicity or a substance having no or little polarity, the sensor according to the second embodiment can detect even such a substance with high sensitivity by detecting the enzymatic reaction inhibitory effect of the target substance.

In the second embodiment, since the acetylcholinesterase aqueous solution is supplied to the reaction unit in a contact state with the target substance, the sensor of the second embodiment can secure a longer time for contact between the acetylcholinesterase and the target substance, as compared with the sensor of the first embodiment in which the acetylcholinesterase and the target substance come in contact with each other in the reaction unit. The longer the time for contact between the acetylcholinesterase and the target substance, the more remarkable the inhibitory effect of the target substance on the acetylcholinesterase, and thus the sensor of the second embodiment is preferable in that the target substance can be detected more sensitively.

Third Embodiment

Figure 6:
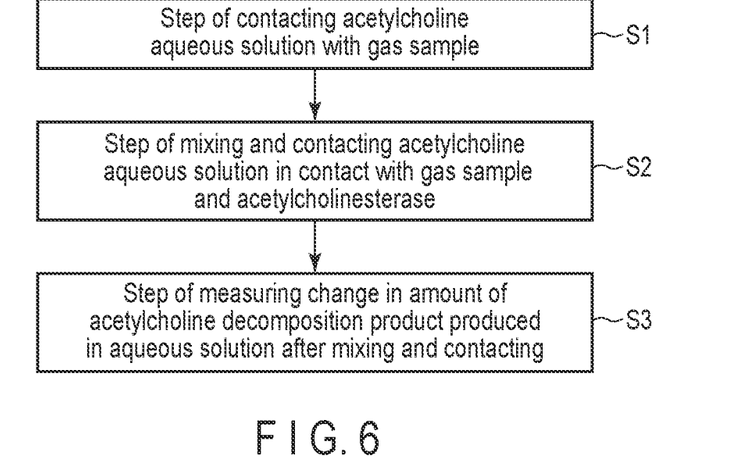
FIG. 6 is a flowchart showing an example of a detection method according to a third embodiment.

A detection method according to the third embodiment will be described in detail with reference to FIG. 6.

The detection method according to the third embodiment includes the following steps. (S1) A step of contacting an acetylcholine aqueous solution with a gas sample, (S2) a step of mixing and contacting the acetylcholine aqueous solution in contact with the gas sample and acetylcholinesterase, and (S3) a step of measuring a change in an amount of acetylcholine decomposition product produced in the aqueous solution after mixing and contacting.

The gas sample is, for example, a gas that is expected to contain the target substance. The gas sample is, for example, the atmosphere, exhaled breath, other gas generated from an analysis target such as a living body or an object, or air around the analysis target, but is not limited thereto.

The target substance is an inhibitor against the acetylcholine decomposition reaction of acetylcholinesterase and is contained in a gas. The target substance includes a biological substance, a non-biological substance, an organic compound, an inorganic compound, or a low molecular weight compound, and for example, odorants, pheromones, fatty acids, hydrocarbons, sulfur oxides, artificial fragrances, or the like. Examples thereof include terpenoids such as limonene, ambrein, and pinene, flavonoids such as luteolin, alkaloids such as galantamine, and glycosides such as Cynatroside A.

In the step S1, when the gas sample contains a target substance due to contact between the acetylcholine aqueous solution and the gas sample, the target substance dissolves in the acetylcholine aqueous solution.

In the step S2, the acetylcholine aqueous solution in contact with the gas sample and acetylcholinesterase are mixed and contacted. When the acetylcholine aqueous solution comes into contact with acetylcholinesterase, the decomposition reaction of acetylcholine proceeds. When the target substance is contained in this mixed system, the decomposition rate of acetylcholine is suppressed. Since acetylcholinesterase acts as a catalyst for reacting specifically or selectively with acetylcholine, it is possible to specifically treat acetylcholine even when the gas sample contains an impurity. As a result, it is possible to identify the type of the product obtained after the treatment.

In the step S3, the change in the amount of acetylcholine decomposition product produced in the aqueous solution after mixing and contacting is measured. The acetylcholine decomposition product is produced by a chemical reaction in which acetylcholine acts as a substrate and acetylcholinesterase acts as an enzyme as described in the formula (1) of the first embodiment. When the target substance is not contained in the gas sample, the amount of acetylcholine decomposition product produced correlates with the amounts of acetylcholine and acetylcholinesterase. On the other hand, when the target substance is contained in the gas sample, the target substance acts as an inhibitor against the enzyme acetylcholinesterase, so that the amount of acetylcholine decomposition product produced decreases. That is, the amount of acetylcholine decomposition product produced when the target substance is contained in the gas sample is smaller than the amount of acetylcholine decomposition product produced when the target substance is not contained.

Due to the inhibitory effect of the target substance on acetylcholine and acetylcholinesterase, a gas sample containing no target substance is determined as a reference sample. Using this sample as the gas sample in the step S1, the amount of acetylcholine decomposition product produced is measured according to the steps S1 to S3, and thereafter, using a gas sample in which the presence of the target substance is unknown, the amount of acetylcholine decomposition product produced is measured according to the steps S1 to S3. Then, when the amount of acetylcholine decomposition product produced in the mixed system contacted with the gas sample in which the presence of the target substance is unknown is different from the amount produced in the mixed system contacted with the reference sample, it is determined that the unknown gas sample contains the target substance. Here, the change in the amount of acetylcholine decomposition product produced between the reference sample and the gas sample in which the presence of the target substance is unknown can be measured as, for example, a change in the pH value, and a change in the current value using a FET based on the pH value.

Therefore, according to the third embodiment, by monitoring the change in the acetylcholine decomposition product in the enzymatic reaction between acetylcholine and acetylcholinesterase, the presence/absence of the target substance in the gas sample and the amount of the target substance according to the magnitude of the change can be detected with high accuracy.

In the third embodiment, steps from S1 to S5 may be continuously carried out without performing another step between any of these steps.

Fourth Embodiment

Figure 7:
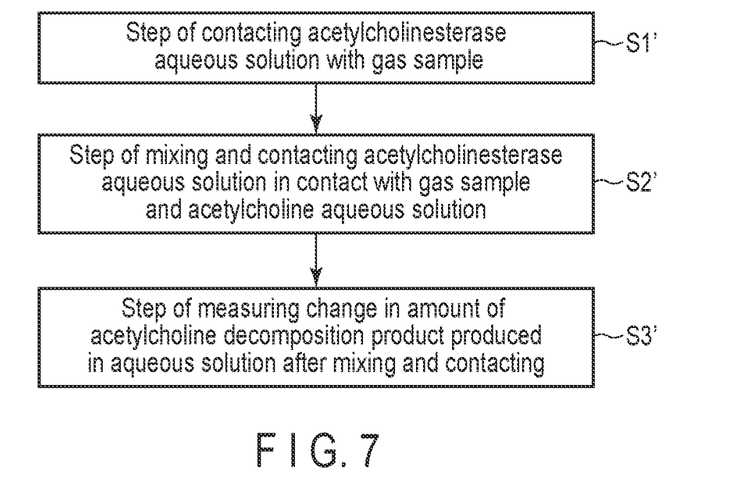
FIG. 7 is a flowchart showing an example of a detection method according to a fourth embodiment.

A detection method according to the fourth embodiment will be described in detail with reference to FIG. 7.

The detection method according to the fourth embodiment includes the following steps. (S1') A step of contacting an acetylcholinesterase aqueous solution with a gas sample, (S2') a step of mixing and contacting the acetylcholinesterase aqueous solution in contact with the gas sample and an acetylcholine aqueous solution, and (S3') a step of measuring a change in an amount of acetylcholine decomposition product produced in the aqueous solution after mixing and contacting.

In the step S1', when the gas sample contains a target substance due to contact between the acetylcholinesterase aqueous solution and the gas sample, the target substance dissolves in the acetylcholinesterase aqueous solution.

In the step S2', the acetylcholinesterase aqueous solution in contact with the gas sample and the acetylcholine aqueous solution are mixed and contacted. When the acetylcholinesterase aqueous solution comes into contact with the acetylcholine aqueous solution, the decomposition reaction of acetylcholine proceeds. When the target substance is contained in this mixed system, the decomposition rate of acetylcholine is suppressed. Since acetylcholinesterase acts as a catalyst for reacting specifically or selectively with acetylcholine, it is possible to specifically treat acetylcholine even when the gas sample contains an impurity. As a result, it is possible to identify the type of the product obtained after the treatment.

In the step S3', the change in the amount of acetylcholine decomposition product produced in the aqueous solution after mixing and contacting is measured. The acetylcholine decomposition product is produced by a chemical reaction in which acetylcholine acts as a substrate and acetylcholinesterase acts as an enzyme as described in the formula (1) of the first embodiment. When the target substance is not contained in the gas sample, the amount of acetylcholine decomposition product produced correlates with the amounts of acetylcholine and acetylcholinesterase. On the other hand, when the target substance is contained in the gas sample, the target substance acts as an inhibitor against the enzyme acetylcholinesterase, so that the amount of acetylcholine decomposition product produced decreases. That is, the amount of acetylcholine decomposition product produced when the target substance is contained in the gas sample is smaller than the amount of acetylcholine decomposition product produced when the target substance is not contained.

Due to the inhibitory effect of the target substance on acetylcholine and acetylcholinesterase, a gas sample containing no target substance is determined as a reference sample. Using this sample as the gas sample in the step S1, the amount of acetylcholine decomposition product produced is measured according to the steps S1' to S3', and thereafter, using a gas sample in which the presence of the target substance is unknown, the amount of acetylcholine decomposition product produced is measured according to the steps S1' to S3'. Then, when the amount of acetylcholine decomposition product produced in the mixed system contacted with the gas sample in which the presence of the target substance is unknown is different from the amount produced in the mixed system contacted with the reference sample, it is determined that the unknown gas sample contains the target substance.

Here, the change in the amount of acetylcholine decomposition product produced between the reference sample and the gas sample in which the presence of the target substance is unknown can be measured as, for example, a change in the pH value, and a change in the current value using a FET based on the pH value.

Therefore, according to the fourth embodiment, as described in the third embodiment, by monitoring the change in the acetylcholine decomposition product in the enzymatic reaction between acetylcholine and acetylcholinesterase, the presence/absence of the target substance in the gas sample and the amount of the target substance according to the magnitude of the change can be detected with high accuracy.

In the Fourth embodiment, steps from S1' to S5' may be continuously carried out without performing another step between any of these steps.

Fifth Embodiment

Figure 8:
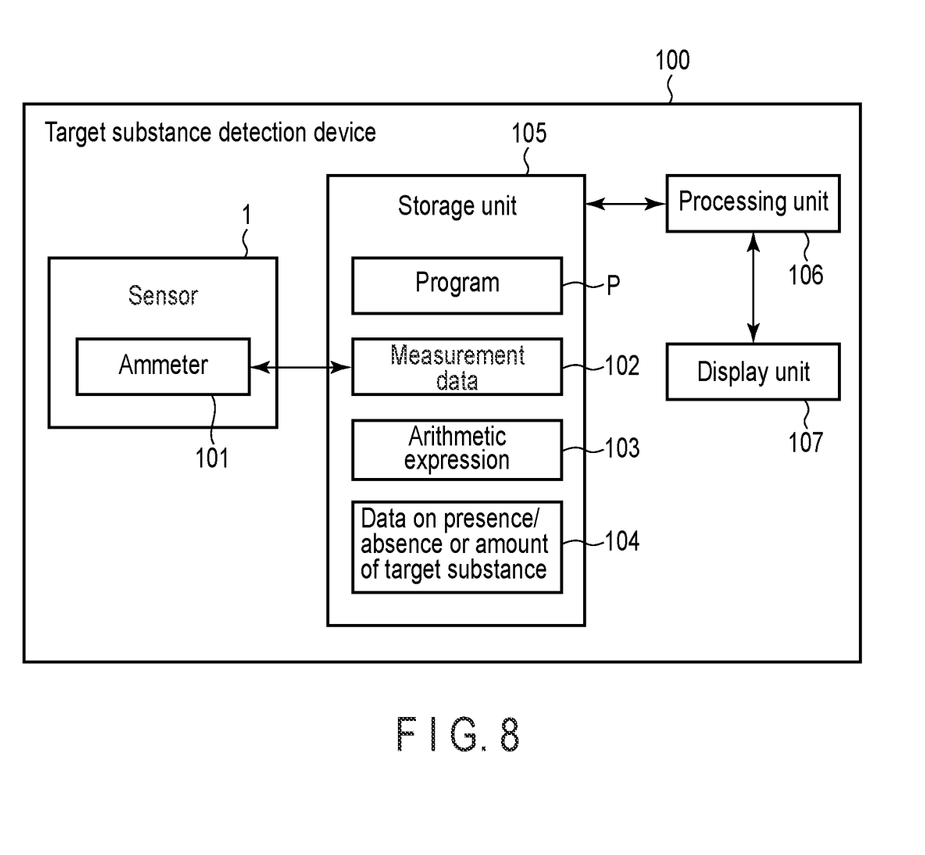
FIG. 8 is a block diagram showing an example of a target substance detection device according to a fifth embodiment.

According to the fifth embodiment, a target substance detection device 100 including a sensor 1 is provided, as shown in FIG. 8. The target substance detection device 100 includes, for example, the sensor 1 provided with an ammeter 101; a storage unit 105 that stores measurement data 102 of a change in an amount of acetylcholine degradation product produced, being measured by the ammeter 101, an arithmetic expression 103 for calculating presence/absence or an amount of a target substance in a sample based on the above data, data on the presence/absence or amount of the target substance 104, a program P, and the like; a processing unit 106 that calculates the presence/absence or amount of the target substance in the sample based on the measurement data 102 and the arithmetic expression 103; and a display unit 107.

According to the target substance detection device 100, for example, a voltage is applied between a source electrode 29 and a drain electrode 31 of the sensor 1, and a current value flowing between the source electrode 29 and the drain electrode 31 when a gas sample containing no target substance is introduced into the sensor 1 as a reference sample, is measured by the ammeter 101. The measurement data 102 of the current value of the reference sample is stored in the storage unit 105. Next, the current value flowing between the source electrode 29 and the drain electrode 31 when a gas sample that may contain a target substance is introduced into the sensor 1 is measured. The measurement data 102 of the current value of the gas sample that may contain the target substance is similarly stored in the storage unit 105. Subsequently, the processing unit 106 takes out the measurement data 102 of the reference sample and the gas sample that may contain the target substance and the arithmetic expression 103 from the storage unit 105, calculates the presence/absence or amount of the target substance 104 in the sample, and then stores the results in the storage unit 105. The processing unit 106 issues an instruction so as to display the presence/absence or amount of the target substance 104 on the display unit 107.

The storage unit 105, the processing unit 106, and the display unit 107 of the target substance detection device 100 may be computers. Each operation of the device may be performed by an input of an operator who performs the detection method, or may be performed by the program P stored in the storage unit.

Sixth Embodiment

According to the sixth embodiment, in a method for detecting a target substance in a sample, a reagent for detecting an inhibitory effect of the target substance on an enzymatic reaction is provided.

The reagent includes a reagent 200 containing acetylcholine and a reagent 201 containing acetylcholinesterase. That is, the reagents 200 and 201 are stored separately. The reagents 200 and 201 further contain a cofactor for acetylcholinesterase as needed.

The reagent 200 or 201 may be provided in the form of a liquid reagent, containing acetylcholine or acetylcholinesterase, respectively, in a suitable solvent. Examples of the solvent include water, physiological water, an ionic liquid, PB buffer, PBS buffer, an organic solvent such as DMSO or alcohol, or a mixture thereof. The concentration of acetylcholine in the liquid reagent is not limited, and is preferably equal to or higher than the Michaelis-Menten constant (a substrate concentration giving half the maximum reaction rate) of the acetylcholinesterase used, for example, several mM.

Further, the reagent 200 may be provided in the form of a powder containing powdered acetylcholine, and the reagent 201 may be provided in the form of a powder containing powdered acetylcholinsterase. In that case, they can be used as liquid reagents by dissolving them in any of the above solvents or the like before use.

The reagent may contain other components as long as it does not inhibit catalytic activity of acetylcholinesterase and does not affect sensor detection. Other components can be, for example, pH regulators, preservatives, stabilizers, and the like. The reagent can be provided in a suitable container.

The reagent is provided, for example, to the sensor of the second embodiment so that the reagents 200 and 201 are held in the container 9 or the liquid storage unit 45 as an acetylcholine aqueous solution or an acetylcholinesterase aqueous solution, respectively.

Seventh Embodiment

According to a further embodiment, a kit including the sensors according to the first or second embodiments and the reagents according to the sixth embodiment is provided.

Although some embodiments of the present invention have been described, these embodiments are presented as examples and not intended to limit the scope of the invention. These novel embodiments can be implemented in various other embodiments, and various omissions, replacements, and changes can be made without departing from the gist of the invention. These embodiments and modifications thereof are included in the scope and gist of the invention, and are also included in the scope of the invention described in the claims and the equivalent scope thereof.

What is claimed is:

1. A sensor for detecting limonene as a target substance in a gas sample, comprising:
    a target substance uptake unit including a container that holds an acetylcholine aqueous solution, wherein the target substance uptake unit brings the acetylcholine aqueous solution in the container into contact with the gas sample to dissolve a target substance in the gas sample into the acetylcholine aqueous solution;
    a reaction unit including a reaction vessel that holds acetylcholinesterase and wherein the reaction vessel is connected to the container of the target substance uptake unit and the reaction unit brings the solution delivered from the target substance uptake unit into contact with the acetylcholinesterase; and
    a detection unit connected to the reaction vessel of the reaction unit, wherein the detection unit measures a change in an amount of acetylcholine decomposition product produced in the solution delivered from the reaction unit.

2. A sensor for detecting limonene as a target substance in a gas sample, comprising:
    a target substance uptake unit including a container that holds an acetylcholinesterase aqueous solution, wherein the target substance uptake unit brings the acetylcholinesterase aqueous solution into contact with the gas sample to dissolve a target substance in the gas sample into the acetylcholinesterase aqueous solution;
    a supply unit including a liquid storage unit that holds an acetylcholine aqueous solution,
    a reaction unit including a reaction vessel connected to the container of the target substance uptake unit and the liquid storage unit of the supply unit, wherein the reaction unit mixes the solution delivered from the target substance uptake unit and the acetylcholine aqueous solution supplied from the supply unit; and
    a detection unit connected to the reaction vessel of the reaction unit, wherein the detection unit measures a change in an amount of acetylcholine decomposition product produced in the solution delivered from the reaction vessel of the reaction unit.

3. The sensor according to claim 1, wherein the acetylcholinesterase is derived from electric eel.

4. The sensor according to claim 1, further comprising a heater for heating the reaction vessel of the reaction unit.

5. The sensor according to claim 1, wherein the detection unit comprises a pH detection element.

6. The sensor according to claim 5, wherein the pH detection element is a sensing element for high mobility measurement.

7. The sensor according to claim 6, wherein the sensing element for high mobility measurement is a graphene FET.

8. A kit comprising the sensor according to claim 1 and a reagent containing acetylcholine and a reagent containing acetylcholinesterase.

9. A kit comprising the sensor according to claim 2 and a reagent containing acetylcholine and a reagent containing acetylcholinesterase.

10. The sensor according to claim 2, wherein the acetylcholinesterase is derived from electric eel.

11. The sensor according to claim 2, further comprising a heater for heating the reaction vessel of the reaction unit.

12. The sensor according to claim 2, wherein the detection unit comprises a pH detection element.

* * * * *